United States Patent
Provot et al.

(10) Patent No.: US 6,261,767 B1
(45) Date of Patent: Jul. 17, 2001

(54) METHOD FOR THE QUALITATIVE AND QUANTITATIVE DETECTION OF DNA DAMAGE

(75) Inventors: Christian Provot, Le Cendre; Bernard Salles, Toulouse; Gilbert Fournie, Toulouse; Patrick Calsou, Toulouse, all of (FR)

(73) Assignee: Societe Francaise de Recherches et d'Investissements (SFRI), Martignas sur Jalles (FR)

( * ) Notice: Subject to any disclaimer, the term of this patent is extended or adjusted under 35 U.S.C. 154(b) by 0 days.

(21) Appl. No.: 08/913,193
(22) PCT Filed: Mar. 13, 1996
(86) PCT No.: PCT/FR96/00391
  § 371 Date: Nov. 25, 1997
  § 102(e) Date: Nov. 25, 1997
(87) PCT Pub. No.: WO96/28571
  PCT Pub. Date: Sep. 19, 1996

(30) Foreign Application Priority Data

Mar. 15, 1995 (FR) .................................................. 95 03230

(51) Int. Cl.$^7$ .............................. C12Q 1/68; C07H 19/00; C07H 21/00; C07H 21/02
(52) U.S. Cl. ............................ 435/6; 435/69.1; 435/91.1; 435/440; 435/325; 514/44; 536/22.1; 536/23.1; 536/23.2; 536/23.4; 536/23.5
(58) Field of Search ............................ 435/6, 69.1, 91.1, 435/440, 325; 514/44; 536/22.1, 23.1, 23.2, 23.4, 23.5

(56) References Cited

FOREIGN PATENT DOCUMENTS

| 0 229 674 | 7/1987 | (EP) . |
| 0 261 955 | 3/1988 | (EP) . |
| 0 472 482 | 2/1992 | (EP) . |
| WO 92/17610 | 10/1992 | (WO) . |

OTHER PUBLICATIONS

Patrick Calsou et al., "Properties of damage–dependent DNA incision by nucleotide excision repair in human cell-free extracts", pp. 4937–4942, Nucleic Acids Research, vol. 22, No. 23, Oxford University Press, 1994.

Patrick Calsou et al., "Measurement of damage–specific DNA incision by nucleotide excision repair in vitro", pp. 788–795, Biochemical and Biophysical Research Communications, vol. 202, No. 2, Jul. 29, 1994.

*Primary Examiner*—Jezia Riley
(74) *Attorney, Agent, or Firm*—Young & Thompson (57) ABSTRACT

A method for the qualitative and quantitative detection of damages to DNA, characterised in that it includes the steps of binding the target DNA to a sensitised substrate, subjecting the DNA to the action of a test composition comprising at least one damage-generating product, subjecting the DNA to the action of a composition containing at least one cell extract active in repairing the DNA and containing markers, and detecting directly or indirectly the markers optionally incorporated into the DNA, if the repair has been effective, wherein a washing step is included between the steps and the binding and damaging steps can be reversed. The invention also provides a method for capturing the DNA directly from the cells with a lysis solution and a method for determining the repair modulation effect of some molecules. The method is suitable for detecting DNA damage and the repair inhibition modulating activity of one or more molecules.

15 Claims, 6 Drawing Sheets

METHOD FOR THE QUALITATIVE AND QUANTITATIVE DETECTION OF DNA DAMAGE

The present invention has for its object a process for the qualitative and quantitative detection of damage to desoxyribonucleic acid due to physical or chemical agents as well as a process for the qualitative and quantitative detection of the activity of modulatory substances for the repair of cellular extracts of damaged DNA.

In the following description and claims, there is referred to as a "damaging product", any pure specific chemical agent, any artificial mixture of chemical agents, or any natural composition of chemical agents or even physical agents such as radiation, particularly ionizing and ultraviolet radiations.

It is known that DNA serve to support the genetic information and that it can be damaged by damaging products with important consequences if the damage is not repaired. Thus, the cellular division is dependent on this information and even the life of the cell is concerned because the genes expressed in the cell are necessary for good cellular functioning.

Also, damage can lead to a mutation of DNA, which can give rise to dysfunction of the cell and as a result introduce a problem into the organism.

It is therefore important to analyze the DNA reactions of an individual as to damaging products so as to get pertinent information, particularly to follow the evolution of certain maladies or for preventing the consequences of them. It is therefore necessary, from cells contained in the blood or in some tissue, to recover DNA then to purify and analyze its behavior with regard to damaging products by determining the consequences induced by this damage.

Thus, in the medical industry, it can be needed to determine qualitatively and quantitatively the genotoxicity or the anti-genotoxicity of a compound or mixture of compounds as to DNA, and if possible the capacities for repairing the damage thus generated. Such a determination is useful as to cells developed and cultivated in vitro or isolated ex vivo. Applications of this type of determination are the detection of genotoxic xerobiotics, following patients in chemotherapy, or following persons working in contact with genotoxic substances.

Another object of the process according to the invention is, in the case of damaging chemical agents, to seek to verify the inhibitory capacities of a compound as to this product, which is particularly the case for oxidants and antioxidants.

There are known different tests concerning DNA and particularly that of patent application EP 0 472 482 in the name of the present applicant, which relates to the dosage with microquantities of DNA present in an extracellular position in a biological liquid, particularly in blood plasma.

This process consists in fixing by adsorption the DNA on a solid support thanks to substances having a high affinity for DNA. Thus, this substance can be chosen particularly from cationic macromolecular complexes.

The solid support is generally a microtitration plate comprising wells, which are sensitized by incubation in a medium containing cationic macromolecular complexes.

This plate is incubated with the specimen whose DNA proportion it is sought to determine. The DNA is adsorbed and the plate is washed in borate buffer with a surfactant or a tris(hydroxymethyl)aminomethane buffer.

The DNA thus fixed is subjected to a molecular biological reaction using several specific enzymes of DNA so as to incorporate at least one nucleotide chemically marked with a substance that can subsequently be detected, for example by enzymatic reaction.

Such incorporation is provided in this process prior to detection by the "Nick translation" reaction, which is to say by a reaction of displacement of haplotomic cutting. Such a marker, described in this previous application, is a modified nucleotide marked with an avidine/enzyme compound or streptavidine/enzyme, the enzyme being peroxidase.

After interruption of the enzymatic reaction, the detection of the incorporated marker is carried out by means of an apparatus adapted to quantify the emitted signal. There is thus measured with a spectrophotometer the colored reaction obtained with biotine.

Such a process of determination of DNA present in very small quantity in a specimen has numerous advantages, particularly:

no extraction of DNA prior to its determination,
no need to use a "hot" marker, which is to say radioactive,
no cumbersome specific apparatus,
high sensitivity,
simultaneous use for more than one hundred specimens, and
obtention of results in several hours.

Such a process therefore has a well determined object which is the determination of DNA so as to determine possible variations of the quantity of DNA, particularly in humans but also under experimental conditions to quantify the phenomena of cellular death.

There is known a test described by Wood et al. [(1988) Cell, 53, 97–106] and Sancar et al. [Sibghat-Ullah et al. (1989) Nucleic Acids Res., 17, 4471–4484], which permits detecting damage to DNA.

This test consists in placing two very pure plasmids of different weights, the one damaged and the other undamaged serving as a reference, in the presence of a cellular extract, transcriptionally active, in the presence among other things of a known composition of dNTP, of marked DATP and of magnesium.

The damage is detected, cut out, and the subsequent reparative synthesis of DNA permits incorporation of radio-marked dNTP whose presence will then be quantified.

A certain percentage of damage is repaired by this incision-excision mechanism and resynthesis, of the order of 7%.

The plasmids are linearized, and caused to migrate on an electrophoresis gel so as to ensure the separation and the radioactive signal emitted by the repaired chains is studied, in which a "hot" marker is present. The signal ratio gives the repair ratio.

The incision-excision activity can also be directly measured [Calsou and Salles (1994) Biochem. Biophys. Res. Comm., 202, 788–795].

Such a test has numerous drawbacks and particularly the fact that the application in industry under satisfactory automated conditions is difficult so that this test is only for laboratories. The delay of obtaining the results, (of the order of two days), is too long and the cost too high. As another drawback, can be cited the requirement to use purified plasmids, of quantities of the order of 200–300 ng and on this subject it should be noted that the test does not seem to be transposable to the analysis of DNA damage in all in vitro or ex vivo sources.

Moreover, it is noted that the markers are isotopes whose manipulation is less easy and that the replacement by markers of another kind is difficult.

Furthermore, in the field of markers, there is a strong tendency to consider that radioactive markers are more sensitive than the others so that researchers are instinctively inclined to use such markers and even to be dissuaded from using cold markers.

Of course tests are known to detect the mutagens because a relationship exists between damage and mutagenesis. These are more particularly the AMES test [Ames et al. (1973) Proc. Natl. Acad. Sci. USA, 70, 2281–2285] complimented by a micronucleus test [Mac Gregor et al. (1987) Mutat. Res. 189, 103–112] which permits the analysis of chromosomic breaks and of tests permitting detecting mutations in genes such as HPRT coding for a biosynthesis enzyme based on DNA.

In the pharmaceutical industry, there is often used and above all in case of doubt about the preceding tests, the UDS test "Unscheduled DNA Synthesis" which consists also in measuring the incorporation of one or several marked nucleotides into DNA of cells subjected to potentially genotoxic agents.

This test has another drawback of involving the manipulation of radio-isotopes and being semi-quantitative.

An improvement of UDS proposed a non-radioactive marker [Selden et al. (1994) Mutat. Res., 315, 147–167], but this is less interesting because the analysis of the results requires the use of flow cytometry, which is a very difficult technique.

The process according to the invention therefore has for its object to overcome the drawbacks of the prior art by permitting qualitatively and quantitatively determining damage in DNA, whether from ex vivo cells (cells, tissues) or in vitro DNA (purified or from cultured cells). The process according to the invention also permits determining the capacity of a substance or of a mixture of substances to inhibit the damaging effect of a damaging product.

The process according to the invention also permits testing modulative repair agents.

Thus, the modulation, more particularly the inhibition of the repair activity of DNA of a cell is of therapeutic route for the treatment of cancers. It is thus sought to develop molecules having properties for inhibiting the repair of DNA.

Also, it would be very useful to test such modules, which would permit screening them rapidly and retaining only the most effective for further study.

It is therefore also an object of the invention to provide for measuring the modulation, by a molecule added to the repair mixture, of the effectiveness of the repair of predamaged DNA, giving a significant repair signal, in the absence of said molecule.

Moreover, the present invention permits by use of a specific supplemental step, treating directly the cells by a damaging chemical product and determining, again qualitatively and quantitatively, the damage suffered by the DNA of said cell.

The process contributes to simplifying this type of study of damage, and can be automated which gives it a certain industrial significance, and it is applicable to all types of DNA and on very small quantities thanks to a very high sensitivity of the test.

The rapidity of the response is also a great advantage, particularly in the industry, because the order of magnitude is of several hours.

The possibility of using "cold" markers and not having to have recourse to "hot" markers whilst maintaining the possibility to do so, is a supplemental advantage. This has for its correlary the use of a specific material for reading, material which corresponds to the incorporated marker but these apparatus are of current usage and relatively simple for one skilled in the art to use, without common measurement with an apparatus of flux cytometry.

Finally, a notable advantage is the possibility of simultaneously analyzing a much larger number of specimens, by a coefficient of about 10.

There will be understood in the following description the following supplemental definitions:

Sensitized support: any support particularly a solid including gelatin, having been treated with substances having a very high affinity for the nucleic material (DNA or RNA).

Cellular extract: partially purified cellular extract, components purified and isolated with if desired recombination in the midst of a composition of certain of these purified components or else a compound obtained by molecular biology.

Marker: Nucleotide modified with a radioactive or non-radioactive marker, of the chemically grafted type.

To this end, the process for a qualitative and quantitative detection of damage to DNA, characterized in that the steps are performed directly on a sensitized support on which damaged DNA is fixed:

action of a composition comprising at least one cellular extract having a repair activity for this DNA, said extract containing markers, direct or indirect revelation of the markers that may be incorporated in the DNA, in case of repair, and comparative reading relative to a control specimen said steps being separated by at least one washing step.

More precisely, the process is characterized in that it comprises the following different steps:

fixation of the DNA target on a sensitized support, action of a composition to be tested comprising at least one damaging product, action of a composition comprising at least one cellular extract having a repair activity on this DNA, said extract containing markers, and direct or indirect revelation of the markers that may be incorporated in the DNA, in case of repair, and comparative reading relative to a control specimen According to another embodiment of use, the steps are the following:

action of a composition to be tested comprising at least one damaging product, fixation of the DNA target on a sensitized support, action of a composition comprising at least one cellular extract having a repair activity on this DNA, said extract containing markers, direct or indirect revelation of the markers that may be incorporated in the DNA, in the case of repair, and comparative reading relative to a control specimen.

The invention also provides a process for measuring the effect of modulation and the inhibitive effect of the repair of at least one molecule, which comprises the following steps:

preparation of damaged DNA fixed on a sensitized support, action of a composition comprising at least one cellular extract having a repair activity on this DNA, said extract containing markers, and conjointly the action of at least one molecule having the power of modulating the repair action, direct or indirect revelation of the markers that may be incorporated in the DNA, in the case of repair, and comparative reading relative to a control specimen.

According to a quite preferred embodiment, the support is a solid support, particularly a microtitration plate with wells or "latex" balls.

The support is sensitized by substances having a very high affinity relative to DNA so as to bring about a securement of this DNA by adsorption.

These substances are selected from cationic substances or proteins, at the pH used for the adsorption of the nucleic material.

The cationic substances are more particularly selected from aminated polyacids of the type of polylysine or polyargine, levorotary, dextrorotary, or levorotary/dextrorotary.

In the case of polylysine, its retained molecular weight is within the fraction 15,000 to 30,000 Daltons.

According to a particular embodiment of use, the sensitization of the support is carried out by incubation in a phosphate buffer 10 mM, sodium chloride 137 mM and a pH comprised between 6.5 and 8, more particularly 7.2.

Preferably, the damaging product, in the case of a chemical damaging product, is diluted in a buffered and bioactive solution.

An example of washing solution is a buffered phosphate solution 10 mM, sodium chloride 137 mM and a nonionic surfactant, for example "Tween 20" in a proportion equal to 0.05 to 0.15% and more particularly 0.1%.

According to the invention, the process can also be practiced for the capture of DNA issued directly from treated living cells and comprises the following steps:
action of a damaging product directly on the cells,
lysis of the cells in a solution,
fixation of the DNA on a sensitized support.

This lysis of the cells in the suitable solution takes place in the presence of the sensitized support.

From treated living cells, the process is characterized also by the following steps:
action of a cellular extract having a repair activity on this DNA, said extract containing markers,
direct or indirect revelation of the markers that may be incorporated in the DNA, in the case of repair, these steps being separated by at least one washing step.

The present process for determining damage to DNA and the associated process for the capture and purification of the DNA for the determination of the damage, as well as the determination of the measure of the modulative effect of the repair, are described hereinafter, with various examples of tests carried out and the results obtained.

The accompanying graphs permit illustrating the description of the process according to the invention in association with the results indicated in the description which follows, and the figures of these drawings show:

FIGS. 1A to 1F, a scheme showing the steps of the process, the FIGS. 1A', 1B' and 1C' corresponding to a modification of the arrangement of certain steps, FIG. 2, graph of the ratio of the proportion of capture of DNA by adsorption in percentage on a rigid support sensitized with polylysine relative to an unsensitized support, FIG. 3, graph of the kinetic of repair of a damaged DNA, FIG. 4, graph of the ratio of repair as a function of the quantity of cellular extract, FIG. 5, graph of the ratio of repair as a function of the concentration of KCl, FIG. 6, graph of the ratio of repair as a function of the different additions of damaging product, in this case ultraviolet rays, FIG. 7, graph of the ratio of repair as a function of the addition of methylmethanesulfonate (MMS) added before or after adsorption of DNA in the well, FIG. 8, graph of the ratio of repair as a function of the dose of 1-methyl-3-nitro-1-nitroso-guanidine (MNNG) incubated with DNA in an organic solvent before adsorption in the well, and FIG. 9, a graph showing the values of the inhibitory effect of different molecules on the repair activity of cellular extracts.

Figure 1A:
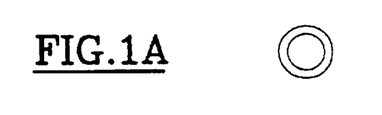
Figure 1B:
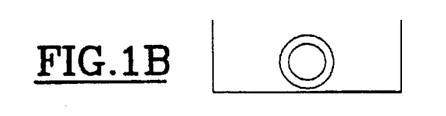

The tests carried out with the aid of the process according to the invention consisted in performing the following steps a/ to f/, shown schematically on FIGS. 1A to 1F and detailed hereafter:

FIGS. 1A–1B: Preparation and Adsorption of DNA on Sensitized Wells a/ A plasmid 2959 bp resistant to ampicillin is prepared by the method of alkaline lysis from *Escherichia coli*, JM109, followed for example, by chromatography on a Quiagen column.

b/ Preparation of a solid support, in this case a microtitration plate with wells of the Microlite II type, sold by the Dynatech company.

The wells of this plate are then sensitized for one night with 50 $\mu$l of poly-L-lysine in the molecular fraction comprised between 15,000 and 30,000 Daltons in a phosphate buffer solution with a salt, this time at a temperature of 4° C.

This plate is washed twice with a washing solution comprising a phosphate buffer with a salt to which is added a non-ionic surfactant, "Tween 20", in a proportion of 0.1%.

For the fixation of DNA on the plate, the solution of DNA is subjected to gentle agitation for 30 minutes at 30° C., then washed twice with a washing solution identical to the washing solution of the plates.

Figure 1C:
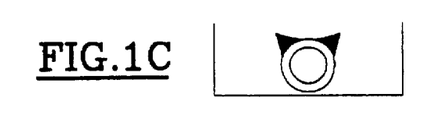

FIG. 1C: Formation of Damage to DNA by the Action of a Damaging Product c/ Generation of damage to DNA thus adsorbed, with a germicidal ultraviolet radiation of 254 nm. The emission rate is measured by a dosimeter for ultraviolet radiation and the radiation is emitted with powers comprised between 50 and 600 $J/m^2$.

Alkalizing agents are diluted in a phosphate buffer 10 mM, to pH 7.2 and incubated with DNA for 1 hour at 30° C.

FIGS. 1A'–1B': Preparation and Action of a Damaging Product on DNA a'/ In a modification, one could reverse the steps of damage and fixation. A plasmid is prepared in a manner identical to that of a/.

b'/ During this phase, damaged DNA is obtained either by incubating in aqueous phase or in an organic solvent of DNA plasmid with at least one genotoxic substance, either by purifying genomic DNA of cells pretreated with at least one genotoxic substance. For example, ethidium monoazide is dissolved in a 10 mM solution of Tris-HCl, 1 mM ethylenediamine tetra-acetic acid and incubated with DNA (80 $\mu$g/ml) with different molar ratios (drug/nucleotide) comprised between $1.10^{-3}$ and $4.10^{-2}$ for 10 minutes and then subjected for 270 seconds to the action of a globe lamp of 500 W.

At the end of this chemical treatment, the DNA is for example precipitated with ethanol.

FIGS. 1C': Adsorption of DNA on Sensitized Wells c'/ In the course of this step, the damaged DNA is fixed in the wells of a sensitized support plate by microtitration in the same manner as in step b/.

The following steps are common to the two embodiments which have been set forth.

Figure 1D:
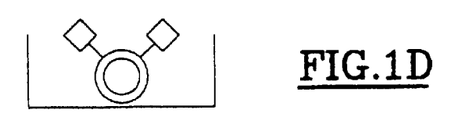

FIG. 1D: Reaction of Repair and Incorporation of DIG-11 dUMP to the Damage Sites, in the Presence of a Cellular Extract d/ Repair in the presence of a cellular extract and of agents of known type, comprising for example for a volume of reaction medium (RM) of 50 µl:

150 µg of proteinic extracts extracted from HeLa cells, 50 mM of KCl in a buffer medium containing 40 mM Hepes-KOH (pH 7.6), 5 mM of $MgCl_2$, 0.5 mM of DTT, 10 mM of phosphocreatine, 2.5 µg of phosphocreatine kinase, 2 mM EGTA, 3.4% glycerol, 18 µg bovine serum albumin, 0.4 µm of dGTP, of dCTP, of DATP and of DIG-11 dUTP.

This repair is obtained by an incubation of 3 hours at 30° C. and the wells are washed three times with the same solution as before.

Figure 1E:
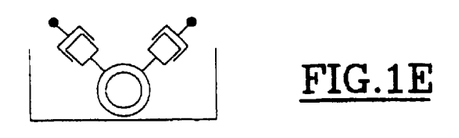

FIG. 1E: Incubation with an Antibody Anti-DIG Conjugated with Alkaline Phosphatase and Verification of Anti-DIG by the Antibody Followed by an Incubation with a Luminescent Agent e/ Marked DNA is incubated 30 minutes with an antibody coupled anti-digoxygenine associated with an alkaline phosphatase diluted to $^{1}/_{10,000}$ in a phosphate buffer with salt, plus 0.025% of acetylated bovine seric albumin and 0.1% of "nonidet P40". The plates are washed three times with the same solution as above.

Figure 1F:
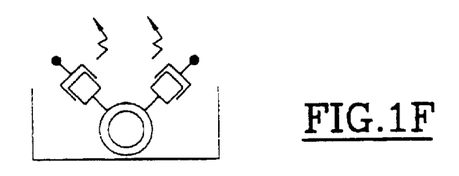

FIG. 1F: Emission of Light Due to Enzymatic Dephosphorylation of "Lumi-Phos 530"

f/ Incubation with a chemiluminescent substrate "Lumi-Phos 530" for 15 minutes and measurement of the light emitted with a luminometer ("Luminoskan") and expressed in relative light units (RLU).

Figure 2:
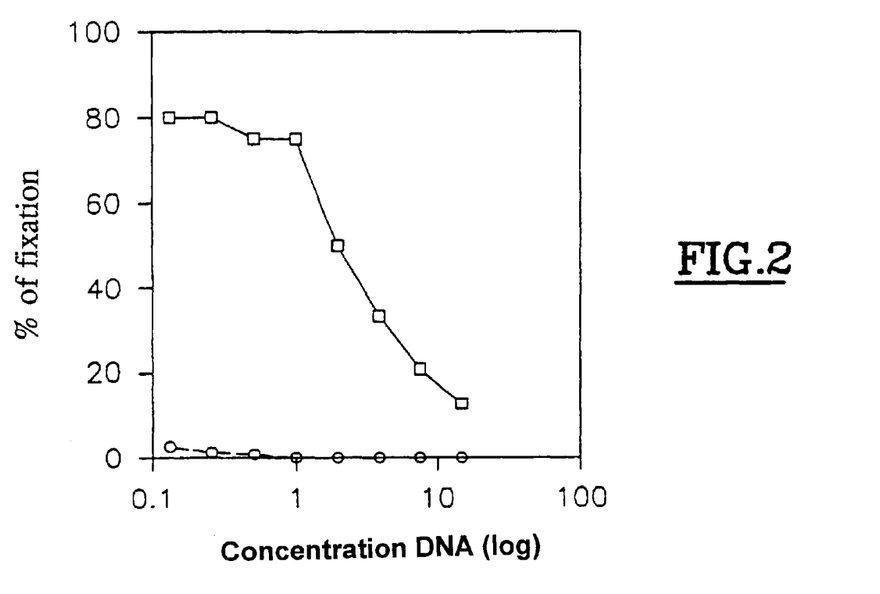

It is noted that the plates sensitized with polylysine permit adsorption of DNA whilst the test plates that are not sensitized do not retain DNA after washing. This is indicated in FIG. 2, on which the curve with the squares represents the percentage of retention of DNA on the plates with polylysine whilst the curve with circles represents the percentage of retention of DNA on the non-sensitized plates.

These curves are obtained by measurement of radioactivity using isotopic markers, during a specific manipulation seeking to determine only the possibilities of retention of DNA. These curves are the mean of three successive trials.

The saturation of the plate with a solution of 50 µl of DNA is achieved with a concentration of 1 to 2 µg/ml of DNA corresponding to sensitization with 40–80 ng of fixed DNA.

Thus, the fixation on a solid support such as a microtitration plate with wells now permits the repair reactions permitting quantifying the capacity of DNA to be repaired, as is now described.

The presence of DNA repairs is detected by the repair reaction by suitable excision in an in vitro medium.

After incubation of the damaged DNA and the undamaged DNA in the presence of a cellular extract, one can determine the ratio of repair by chemiluminescence.

In all the figures showing the condition of a repair ratio, the latter is defined as the ratio of the raw luminescence signal obtained for a "test" condition on the signal obtained with untreated control DNA.

The tests consisted in varying the following parameters: time of incubation, importance of the damage, concentration of cellular extract, concentration of salt, or quantity of DNA, so as to optimize the repair reaction.

Figure 3:
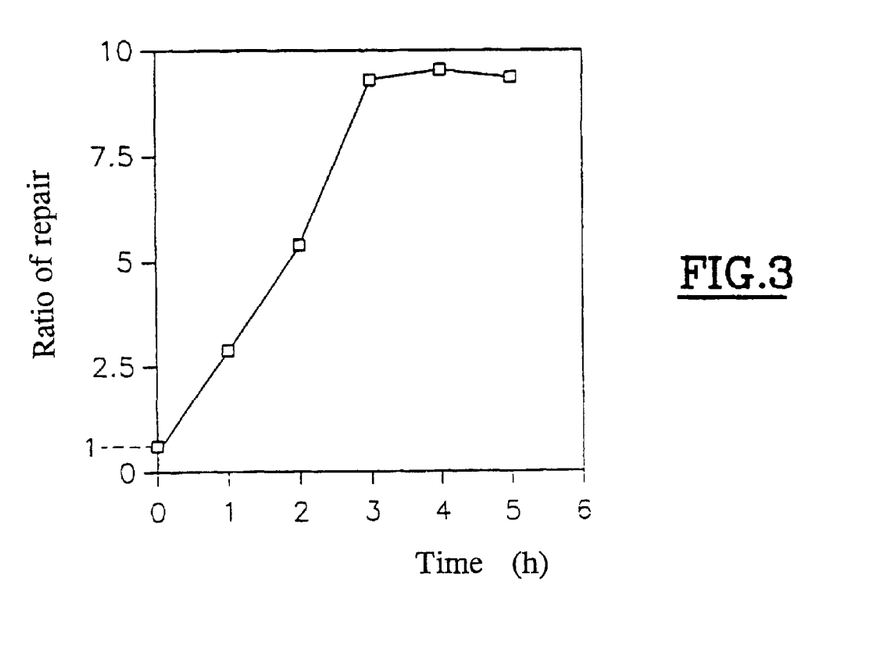

Thus, the kinetics of repair with a cellular HeLa extract, shown by the graph of FIG. 3, show that the maximum repair is obtained in three hours, at the end of which the repair kinetic stabilizes.

Figure 4:
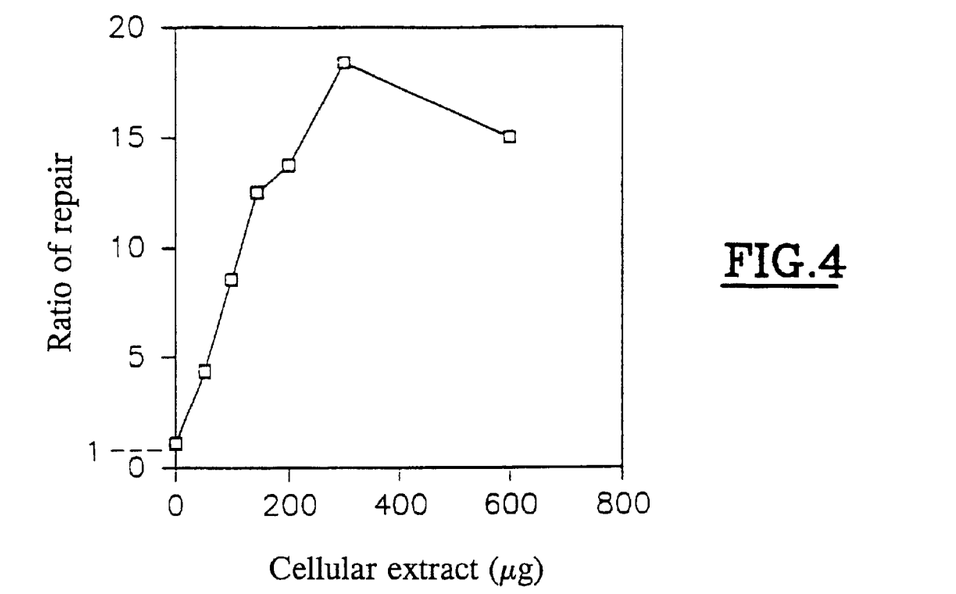

Thus, with a DNA having been subjected to a dose of 300 $J/m^2$ of ultraviolet radiation, the maximum of synthesis of repair of damage is obtained in the presence of 300 µg of cellular extract, as is shown by FIG. 4.

Figure 5:
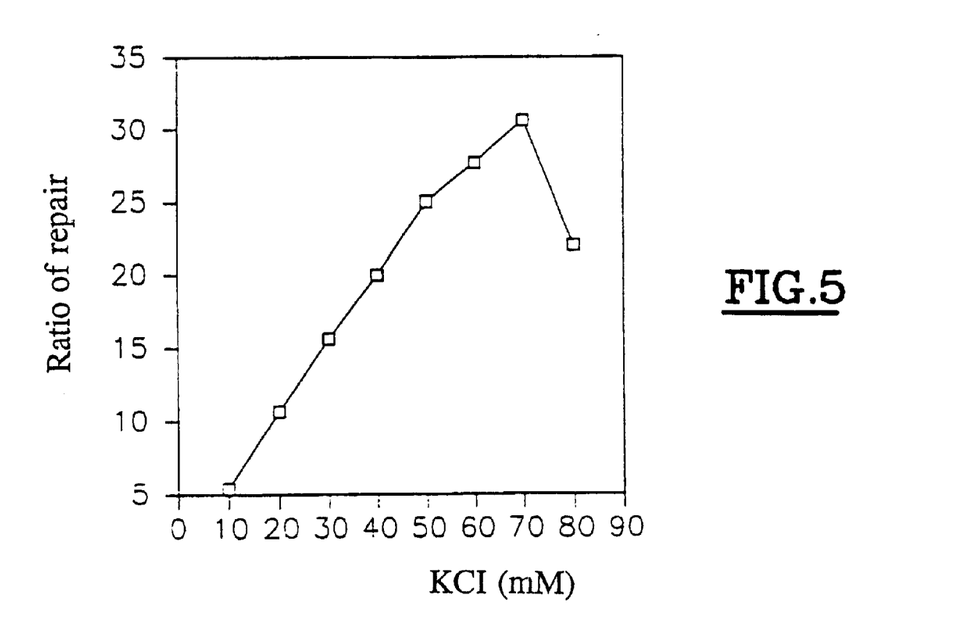

So as further to optimize the repair synthesis, FIG. 5 shows tests with different concentrations of salt, in this instance potassium chloride, KCl. The curve shows a maximum at 70 mM of KCl.

As a result of the tests, the optimum values obtained are:

duration of incubation: 3 hours, quantitative cellular extract: 150 µg, and 70 mM of KCl.

The process according to the invention then consists in revealing the damage thus generated and two possibilities are offered, the first in which the damage is generated prior to the adsorption step and the second in which the damage is generated after the adsorption step.

Figure 6:
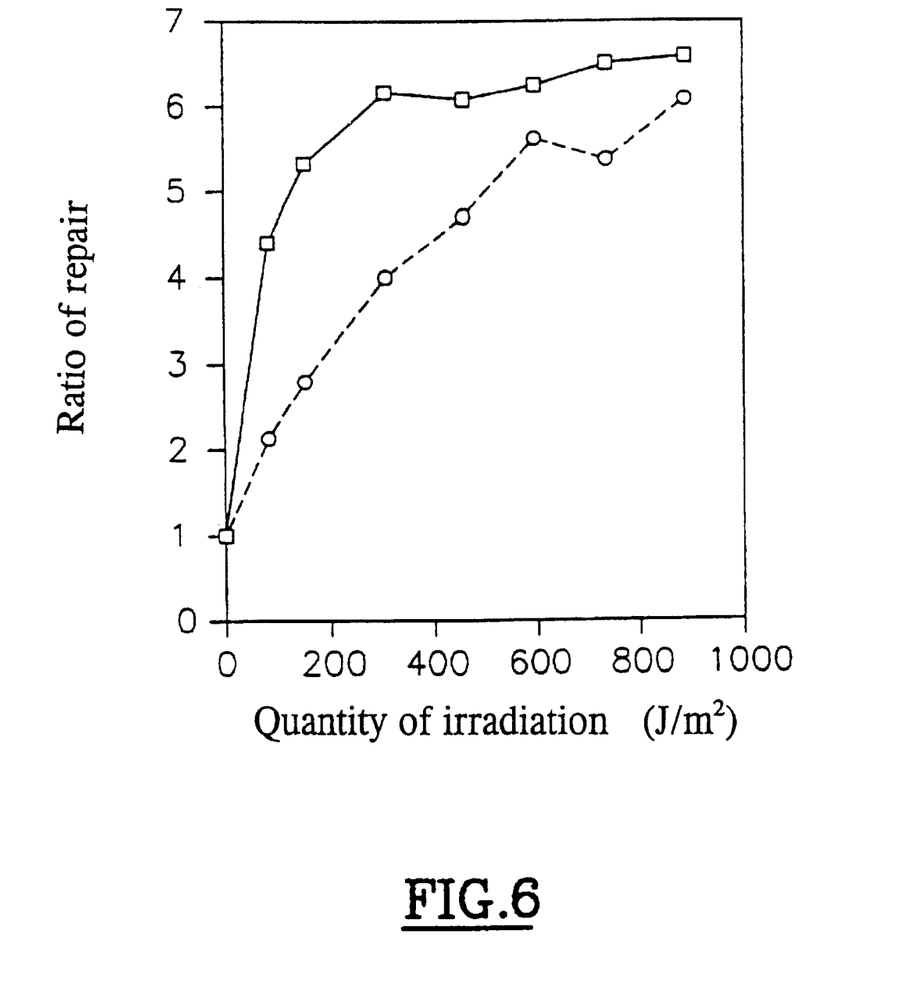

In FIG. 6, the curve with squares corresponds to subjecting the DNA to ultraviolet radiation before the adsorption step and the curve with circles corresponds to subjecting the DNA to ultraviolet radiation after the adsorption step.

Similar results have been found as concerns the ratio of repair of the damage.

In a complementary way, other tests have been conducted by using as damaging product genotoxic compounds which lead particularly to the formation of adducts.

Figure 7:
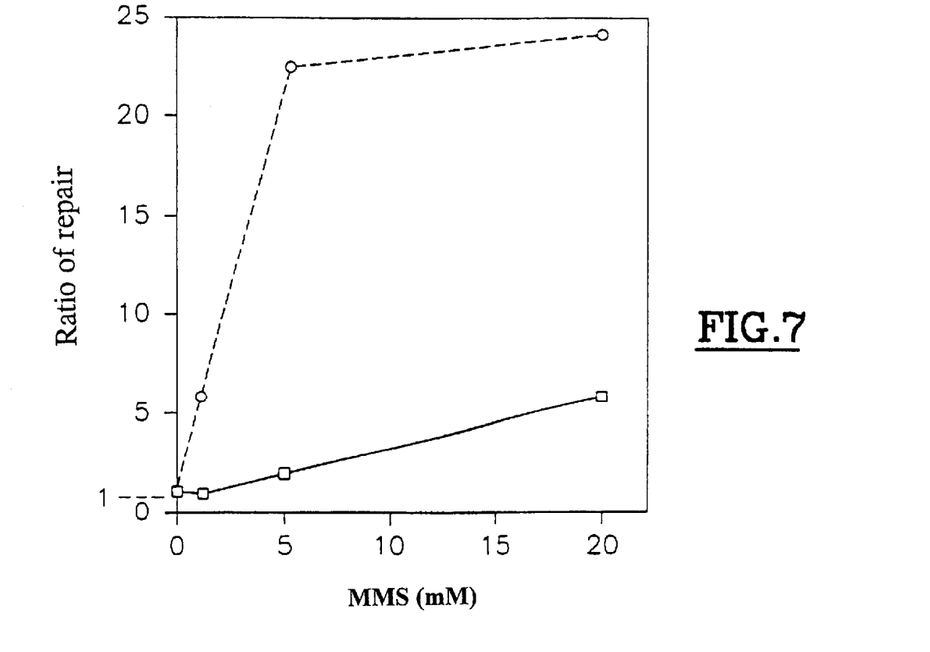
Figure 8:
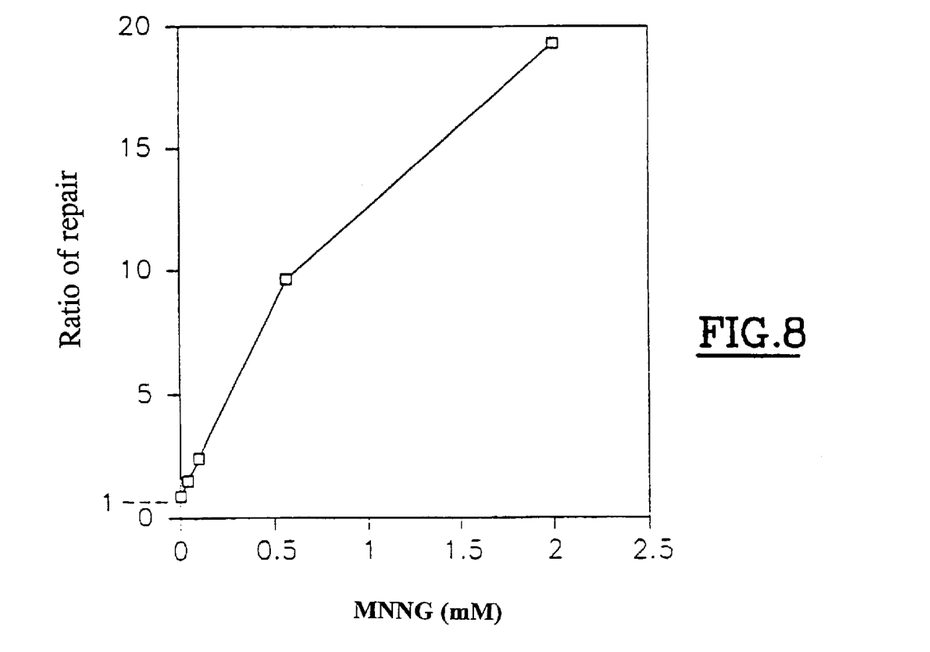

In the same way as for the treatment of DNA with UV rays, the formation of damage of the adduct type detected by the test according to the invention can have been produced in DNA adsorbed in the wells or preliminarily to adsorption as is shown in FIGS. 7 and 8.

In FIG. 7, DNA was treated with an alkalizing agent, methylmethanesulfonate (MMS), which induces damage by covalent fixation.

In the case of the curve with squares, DNA was treated once it was adsorbed in the wells and in the case of the curve with circles, the DNA was preliminarily treated in liquid phase with MMS and then adsorbed in the wells.

It will be seen that in this example, placing the DNA in contact with MMS before the adsorption step permits a greater effectiveness of damage as shown by the repair ratio.

In FIG. 8, there is tested the effect-dose of 1-methyl-3-nitro-l-nitroso-guanidine (MNNG), a known genotoxic agent, as a reference. In this case, the DNA target was preincubated with increasing quantities of MNNG dissolved in dimethylsulfoxide (DMSO). This shows that this genotoxicity can be detected in a dose-dependent fashion.

It will be noted that the process on a plate according to the invention is a test of high sensitivity because the detection is carried out with 40 ng of DNA instead of 200 to 300 ng, in the case of working in a tube.

Moreover, the test according to the invention can be automated.

This same test can also be used to screen the genotoxic compounds, certain of them being adapted to be activated by enzymes. Similarly, the action of oxidizing compounds can be tested as the inhibition effect of antioxidant agents.

Tests have been conducted with damage generated by two types of oxidizing agents:

hydrogen peroxide $H_2O_2$, methylene blue.

a/ Hydrogen peroxide is known to produce free radicals by the FENTON reaction. Microtitration plates with wells comprising fixed DNA are incubated for different periods of time with variable quantities of hydrogen peroxide diluted in phosphate buffer solution at 37° C. Tests have shown that the maximum ratio of repair is obtained for a quantity of 0.27 mM of hydrogen peroxide, namely a dilution of $1.6 \times 10^{-4}$ of 30% $H_2O_2$. The plates are then rinsed twice with the same washing solution as before, utilizing the non-ionic surfactant "Tween 20" in the amount of 0.1%.

b/ Methylene blue is known to liberate by photo-activation, one atom of oxygen.

For the tests to follow, methylene blue was subjected to radiation with visible light for 20 minutes with two bulb lamps of 100 W, a distance between the lamps and the support plates of 30 cm and a concentration of methylene blue of 50 ng/ml.

The step of repair of the damage is carried out according to the information indicated above, with the use of the same reaction medium RM.

In the same fashion, the plates, after the action of the reaction medium RM are washed three times with the washing solution indicated above, and incubated 15 minutes with a chemiluminescent substrate ("Lumi-Phos 530").

Knowing the actions of such oxidants on DNA, the tests have permitted testing the effectiveness of antioxidant compounds by analyzing the luminescence corresponding to the repair which must be the less the more effective is the antioxidant.

For the first test, as the production of free radicals from hydrogen peroxide requires the presence of iron, there has been used a metallic chelating agent, mesylate deferroxamine, so as to verify whether the production of damage could be inhibited. It has been determined that 10 μm of this metallic chelating agent inhibits totally the effects of the hydrogen peroxide.

For the second test, with methylene blue, the relative activity RA has been calculated of an antioxidant which is equal to:

$$RA = \frac{(\text{control } RLU - \text{test } RLU)}{(\text{control } RLU - \text{reference } RLU)}$$

in which formula:

control RLU corresponds to the value of the signal of methylene blue alone subjected to radiation, test RLU corresponds to the value of the signal of methylene blue subjected to ultraviolet radiation plus an antioxidant molecule, and reference RLU corresponds to the value of the signal of the antioxidant molecule alone.

Calculations show, as is given in the following table, that silymarine has a high antioxidant activity whilst plasma and vitamin A have no antioxidizing effect.

| silymarine (mM) | R.A. (with MB) | R.A. (with $H_2O_2$) | Vitamin C (μM) | R.A. (with MB) | R.A. (with $H_2O_2$) |
|---|---|---|---|---|---|
| $10^{-5}$ | 0.44 | ND | $10^{-5}$ | 0.22 | 0.12 |
| $10^{-4}$ | 0.47 | ND | $10^{-4}$ | 0.39 | 0.20 |
| $10^{-3}$ | 0.43 | ND | $10^{-3}$ | 0.21 | 0.19 |
| $10^{-2}$ | 0.49 | ND | $10^{-2}$ | 0.24 | 0.30 |
| $10^{-1}$ | 0.94 | 0.66 | $10^{-1}$ | 0.28 | 0.45 |
| 1 | 1 | 1 | 1 | −1.2 (a) | 0.56 |

| Vitamin A (μM) | R.A. (with MB) | R.A. (with $H_2O_2$) | Plasma (dilution) | R.A. (with MB) | R.A. (with $H_2O_2$) |
|---|---|---|---|---|---|
| $10^{-4}$ | 0.07 | 0.06 | $3.10^{-6}$ | 0 | 0 |
| $10^{-3}$ | 0.24 | 0.15 | $1.10^{-5}$ | 0.07 | 0.40 |
| $10^{-2}$ | 0.25 | 0.20 | $2.10^{-5}$ | 0.12 | 0.69 |
| $10^{-1}$ | 0.14 | 0.21 | $5.10^{-5}$ | 0 | 0.85 |
| 1 | 0.21 | 0.18 | $2.10^{-4}$ | 0 | 0.95 |
| 10 | 0.18 | 0.20 | $4.10^{-4}$ | 0 | 0.98 |

(a) a negative value indicates that the test value is greater than the reference value
ND: not determined
MB: methylene blue In the course of the repair step, see FIG. 1D, the molecules for which it is sought to show a modulator effect of the repair can be added. These molecules are preferably diluted in water or in dimethylsulfoxide (DMSO).

Figure 9:
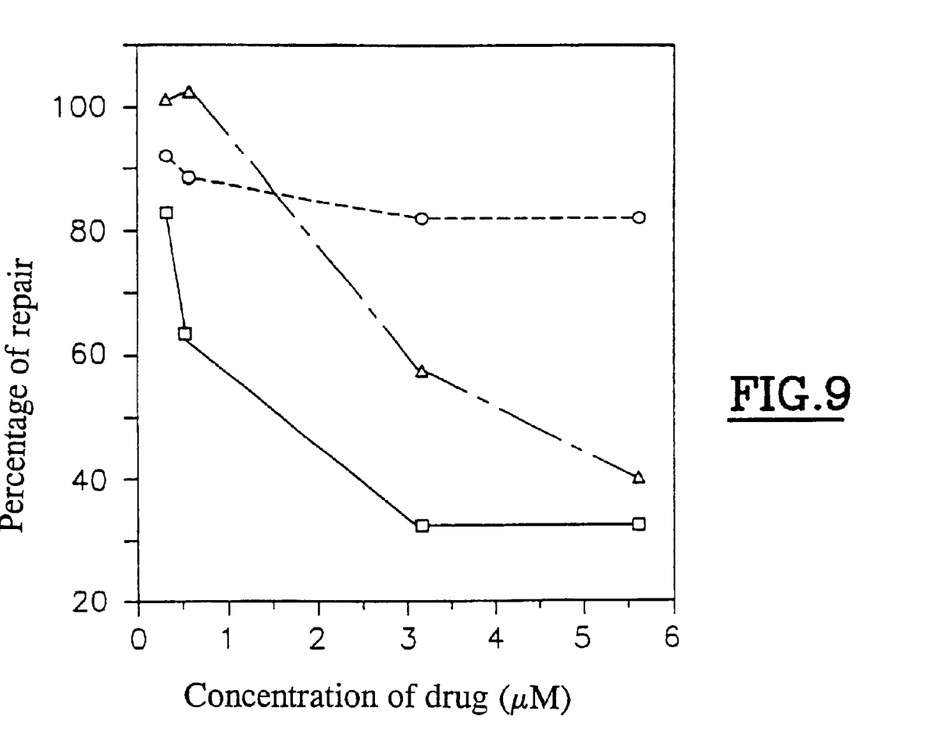

In FIG. 9, there is shown the measure of the dose-dependent inhibitor effect of the repair by two poison antitumor molecules of topoisomerase II, namely actinomycin D (curve with squares) and doxorubicine (curve with triangles) on the extracts from HeLa cells.

On the contrary, nalidixic acid, an inhibitor of the subunit gyrA of gyrase of *E.coli* (curve with circles) is without effect on the activity of these extracts from HeLa cells.

This shows that by means of the process according to the invention, in a simple and above all very rapid fashion, can be tested the effect of a particular agent or the combination of agents modulating the repair activity of cellular extracts.

DNA can thus be directly detected from cells having been subjected to the action of a compound adapted to induce damage in DNA of these cells, for example a genotoxic agent, or a mixture of compounds.

Among these compounds can be cited the oxidizing products because they generate free radicals of the singlet oxygen type $^1O_2$, and the hydroxyl radical $OH^•$, as that has been indicated when the tests are produced directly on DNA fixed on a solid support.

Proceeding in the same fashion as above for the analysis of damage and detection, the problem posed is the detection of DNA.

According to the invention, the cells are therefore subjected to the action of the compound to be tested, for example a genotoxic agent, then, after a variable incubation period, in the presence of this genotoxic agent, the cells are incubated in the presence of a lysis agent directly in the wells of a sensitized microtitration plate, so as to capture the DNA thus generated, which must be analyzed.

There can be cited as lysis composition a solution in a phosphate buffer 10 mM, sodium chloride 137 mM, urea 5 to 20% (preferably 10%), hexadecyltrimethyl ammonium bromide 0.1 to 0.5% (preferably 0.2%), proteinase K, 200 to 500 μg/ml. 5 The step of lysis is comprised between 30 minutes and 2 hours.

It has thus been possible to fix DNA on a solid support, concomitantly to the lysis of the cells, and this DNA can then be subjected to any analysis requiring its placement on a support.

In particular, the damage can be analyzed by applying to this DNA the step of repair and cold or hot marking and the step of quantitative and qualitative revelation, as have been described above in this text.

In this case, the washings are effected in the same manner as above, with a suitable solution, then the wells of the plate are incubated with a cellular extract so as to permit eventual repair.

The revelation, particularly by chemiluminescence in the case of recourse to cold markers of this type, permits studying the damage generated in DNA when the cell which carries it is subjected to the action of a compound to be tested.

This process of capture and securement of DNA on a solid support is useful for numerous applications.

Thus, it is applicable more generally:

to the capture and purification of DNA or RNA so as to amplify enzymatically the particular nucleotide sequences, to the capture of DNA of cells subjected to genotoxic agents for analysis by a UDS test with a cold marker or else, to the capture and analysis of fragments of DNA from cells subjected to chemical or physical stress.

Such a procedure has interest taken alone and more particularly in the case of the analysis process indicated above. It should be noted that it requires a small quantity of initial material; thus the DNA genome from $10^4$ to $10^5$ cells can be detected and the damage quantified when the cell has been treated by any genotoxic substance.

What is claimed is:

1. Process for qualitatively and quantitatively detecting damage to DNA, which comprises the steps of:

subjecting the DNA to the action of a composition containing at least one cellular extract having repair activity for said DNA, said extract containing markers;

detecting directly or indirectly the markers that may be incorporated in the DNA, in the case of repair;

obtaining comparative reading with respect to a control sample; and wherein said steps are carried out directly on a sensitized support on which damaged DNA is fixed, said steps being separated by at least one step of washing which uses a washing solution comprising 10 mM Phosphate buffer, 137 mM sodium chloride, and a non-ionic surfactant.

2. Process for qualitatively and quantitatively detecting damage to DNA, which comprises the following sequential steps:

fixing the DNA target on a sensitized support;

subjecting the DNA target to the action of a test composition comprising at least one damage-generating product, said damage-generating product being a chemical damaging product diluted in a buffered solution;

subjecting the DNA to the action of a composition containing at least one cellular extract having repair activity for said DNA, said extract containing markers;

detecting directly or indirectly the markers that may be incorporated in the DNA, in the case of repair; and obtaining a comparative reading relative to a control specimen.

3. Process for qualitatively and quantitatively detecting damage to DNA, which comprises the following sequential steps:

subjecting the DNA to the action of a test composition comprising at least one damage-generating product, said damage-generating product being a chemical damaging product diluted in a buffered solution;

fixing the DNA target on a sensitized support;

subjecting the DNA to the action of a composition containing at least one cellular extract having repair activity for said DNA, said extract containing markers;

detecting directly or indirectly the markers that may be incorporated in the DNA, in the case of repair; and obtaining a comparative reading relative to a control specimen.

4. Process for measuring the modulating effect of repair of at least one molecule, which comprises the following steps:

preparing damaged DNA by fixing on a sensitized support;

subjecting the DNA to the action of a composition containing at least one cellular extract having repair activity for said DNA, said extract containing markers, and conjointly to the action of at least one molecule adapted to have a modulating power on the repair;

detecting directly or indirectly the markers that may be incorporated in the DNA, in the case of repair; and determining the modulator effect of said molecular by obtaining a comparative reading relative to a control specimen.

5. The process according to claim 1, wherein the support is a solid support.

6. The process according to claim 5, wherein the solid support is a microtitration plate with wells or latex balls.

7. The process according to claim 1, wherein the support is sensitized by substances having a very high affinity for DNA so as to effect a securement of said DNA by adsorption.

8. The process according to claim 7, wherein the substances are selected from cationic and protein substances, at the pH used for adsorption of nucleic material.

9. The process according to claim 7, wherein the substances are levorotary, dextrorotary, or levorotary/dextrorotary cationic substances, and are selected from aminated polyacids of the polylysine or polyargine type.

10. The process according to claim 9, wherein the cationic substance is polylysine having a retained molecular weight located in the fraction 15,000 to 30,000 Daltons.

11. The process according to claim 8, wherein the support sensitized by incubation in a 10 mM phosphate buffer with 137 mM sodium chloride at a pH ranging between 6.5 and 8.

12. The process according to claim 11, wherein the pH is 7.2.

13. The process according to claim 2, wherein the damage-generating product is a chemical damaging product which is bioactivated.

14. The process according to claim 3, wherein the damage-generating product is a chemical damaging product which is bioactivated.

15. The process according to claim 1, wherein the non-ionic surfactant is TWEEN 20 in a proportion equal to 0.05 to 0.15 weight percent.

* * * * *